United States Patent [19]

Fleenor

[11] Patent Number: 5,330,469

[45] Date of Patent: * Jul. 19, 1994

[54] APPARATUS FOR SUPPORTING AN ELECTROSURGICAL GENERATOR AND INTERFACING SUCH WITH AN ELECTROSURGICAL PENCIL AND AN INERT GAS SUPPLY

[75] Inventor: Richard P. Fleenor, Denver, Colo.

[73] Assignee: Beacon Laboratories, Inc., Broomfield, Colo.

[*] Notice: The portion of the term of this patent subsequent to Aug. 20, 2008 has been disclaimed.

[21] Appl. No.: 681,082

[22] Filed: Apr. 5, 1991

Related U.S. Application Data

[63] Continuation-in-part of Ser. No. 377,528, Jul. 10, 1989, Pat. No. 5,041,110.

[51] Int. Cl.[5] .................................. A61B 17/36
[52] U.S. Cl. ............................. 606/40; 606/34
[58] Field of Search .......................... 606/10–13, 606/23, 27, 28, 32–40, 17–20

[56] References Cited

U.S. PATENT DOCUMENTS

| | | | |
|---|---|---|---|
| 2,510,205 | 6/1950 | Baird | 219/8 |
| 2,618,267 | 11/1952 | Hanriot | 128/303.14 |
| 2,708,933 | 5/1955 | August | 128/303.14 |
| 2,828,747 | 4/1958 | August | 128/303.14 |
| 3,578,939 | 5/1971 | Green | 219/74 |
| 3,834,392 | 9/1974 | Lampman et al. | 128/303.13 |
| 4,040,426 | 8/1977 | Morrison, Jr. | 128/303.17 |
| 4,060,088 | 11/1977 | Morrison, Jr. et al. | 128/303.17 |
| 4,072,152 | 2/1978 | Linehan | 128/303.1 |
| 4,100,390 | 7/1978 | Jackson | 219/74 |
| 4,196,734 | 4/1980 | Harris | 128/303.1 |
| 4,209,018 | 6/1980 | Meinke et al. | 128/303.17 |
| 4,562,838 | 1/1986 | Walker | 128/303.14 |
| 4,573,466 | 3/1986 | Simada et al. | 128/303.1 |
| 4,640,279 | 2/1987 | Beard | 128/303.14 |
| 4,781,175 | 11/1988 | McGreevy et al. | 128/303.17 |
| 4,901,720 | 2/1990 | Bertrand | 606/40 |

OTHER PUBLICATIONS

"The Argon Beam Coagulator. A User Experience Profile." Bard Electro Medical Systems, Inc.

Primary Examiner—Danton D. DeMille
Assistant Examiner—Sam Rimell
Attorney, Agent, or Firm—Sheridan, Ross & McIntosh

[57] ABSTRACT

An apparatus for supporting an electrosurgical generator (14) and interfacing the generator (14) with an electrosurgical pencil (40, 234, or 254) and a supply of inert gas to allow gas-enhanced electrosurgery. One embodiment generally includes an accessible platform (134) for supporting the generator (14), a receiving area (146) for containing a supply of inert gas, an adaptor (142) for receiving an electrosurgical pencil interconnected with the supply of inert gas, and an interface structure (210) which allows an operator, through use of a control device, to control the flow of gas and electrical output to the pencil. Consequently, existing generators may be used with the present invention to conduct gas-enhanced electrosurgery.

28 Claims, 11 Drawing Sheets

APPARATUS FOR SUPPORTING AN ELECTROSURGICAL GENERATOR AND INTERFACING SUCH WITH AN ELECTROSURGICAL PENCIL AND AN INERT GAS SUPPLY

RELATED APPLICATIONS

This application is a continuation-in-part application of co-pending application for U.S. patent Ser. No. 07/377,528, filed Jul. 10, 1989, U.S. Pat. No. 5,041,110 and entitled "METHOD AND APPARATUS FOR MOBILIZING AN ELECTROSURGICAL GENERATOR AND INERT GAS SYSTEM."

TECHNICAL FIELD OF THE INVENTION

This invention relates in general to electrosurgical devices, and in particular to an apparatus for supporting an electrosurgical generator and for conveniently allowing for the use of an inert gas and electrosurgical pencil with the generator.

BACKGROUND OF THE INVENTION

Electrosurgical generators have long been used for the control of bleeding and for making incisions in major surgery. Currently, there are approximately 22 million surgeries conducted every year in the United States, and of those 22 million roughly 18 million are conducted using electrosurgical techniques. The use of electrosurgical generators requires that an electrosurgical pencil be interconnected to the generator. An electrosurgical pencil comprises an insulated handle with an electrode therein for passing an electric charge to a patient. The generator provides a source of electric current to the electrode of the pencil which is then used, for example, to cut tissue or coagulate blood.

Unfortunately, the use of electricity in a surgical environment has occasionally caused serious injury to the patient and the surgical personnel. When anesthetics commonly used were of a flammable or explosive nature, the uncontrolled emission of electric current often ignited the anesthetic. Since anesthetics are generally no longer flammable, the risk of their ignition has been greatly reduced.

It has been found that the use of an inert gas (such as Argon) tends to enhance, rather than merely insulate, the flow of electricity in electrosurgery through ionization of the inert gas atoms. Inert gas-enhanced electrosurgery allows coagulation without excessively drying tissue, and thus is a valuable surgical tool. However, gas enhancement is a substantially untapped surgical resource due to the lack of a device that combines the inert gas with the electric charge.

The current state of the art reflects the use of electrosurgery generally without the use of an enhancing inert gas, although there are a variety of types of electrosurgical generators and electrosurgical pencils currently available. The generators are typically separate units that are placed on tables or stands in the operating room. However, there has been no device that allows the adaptation of the existing generators for use with inert gas for gas-enhanced electrosurgery. One device (System 6000 by Birtcher Electro Medical Systems, Inc.) does combine an inert gas supply and generator for electrosurgery but does not generally meet the needs of the industry. Thus, there is a need for an apparatus to support an electrosurgical generator and allow inert gas-enhanced electrosurgery using an existing generator.

SUMMARY OF THE INVENTION

The present invention disclosed herein comprises an apparatus for supporting an electrosurgical generator and combining therewith the benefits of inert gas enhancement. The present invention allows the convenient consolidation of a multiplicity of parts needed to conduct electrosurgery with an inert gas.

One embodiment of the present invention generally includes a support structure which has an accessible platform for supporting an electrosurgical generator and facilities for fluidly receiving and storing a supply of inert gas for use with an electrosurgical pencil which is connectable to the support structure. A control mechanism is operatively connected to the electrosurgical pencil, which itself is interconnected with the supply of inert gas, to control the provision of inert gas and electrical output thereto during performance of gas-enhanced electrosurgery. More particularly, the control mechanism is operatively connected to an interface structure within the support structure such that when the control mechanism is activated by the operator, a signal is sent to the interface structure to initiate the provision of inert gas to the electrosurgical pencil. The control mechanism is also operatively connected to the electrosurgical generator such that when the operator activates the control mechanism, electrical output is also provided to the electrosurgical pencil via a connection between the generator and pencil. Consequently, the present invention possesses features which allow an electrosurgical generator to be used in performing gas-enhanced electrosurgery.

In one embodiment of the present invention, the support structure has a plurality of wheels or rollers attached to the bottom portion thereof. Consequently, the size of the support structure can be increased to a certain degree without significantly affecting the overall mobility of the entire assembly. With the increased size of the support structure, certain additional features may also be provided if desired. For instance, the receiving area for the supply of inert gas may be configured such that one or more inert gas storage tanks may be positioned therein in upstanding fashion and so that the tanks are easily accessible for installation and removal procedures. Furthermore, a control valve assembly may be incorporated which will allow the operator to select from a plurality of flow rates of inert gas to be provided to the electrosurgical pencil.

In another embodiment of the present invention, the support structure is designed to be a portable unit which may be easily transported between locations for use on a table top, cart or other horizontal surface. As a result of the reduced size of the support structure, the space available for the receiving area for the supply of inert gas may be limited such that only a single inert gas storage tank may be contained within the support structure in a horizontal position. However, a detachably connectable single flow rate control valve may be incorporated such that the operator may still select a desired flow rate of inert gas to the electrosurgical pencil by selecting a control valve having the desired orifice size.

A key feature of the present invention is the interface achieved between the electrosurgical generator and a supply of inert gas so that gas-enhanced electrosurgery is achievable. The present invention provides a number of options for achieving this interface and for controlling the flow of gas and electricity by having features which allow a variety of electrosurgical pencils to be used therewith. For instance, in one embodiment the control mechanism is a foot-activated control which is interconnected to the electrosurgical generator through the interface structure by means of a foot plug on the support structure. By activating the foot control, the operator is able to initiate the simultaneous provision of inert gas and electrical output to the electrosurgical pencil. In another embodiment the control mechanism is a single control switch positioned on the electrosurgical pencil which functions similarly to the foot-activated switch by being electrically connected to the interface structure. In still another embodiment the control mechanism includes two switches positioned on the electrosurgical pencil. The first switch is directly electrically connected to the electrosurgical generator and when activated, it initiates the provision of electrical output to the pencil at a first level. The second switch is also directly electrically connected to the generator such that when depressed to a first stage, it initiates the flow of electrical output to the pencil at a second level. However, the second switch is also operatively connected to the interface structure such that when depressed to a second stage, a signal is sent to the interface structure to initiate the provision of inert gas to the pencil.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION OF THE INVENTION

Figure 1:
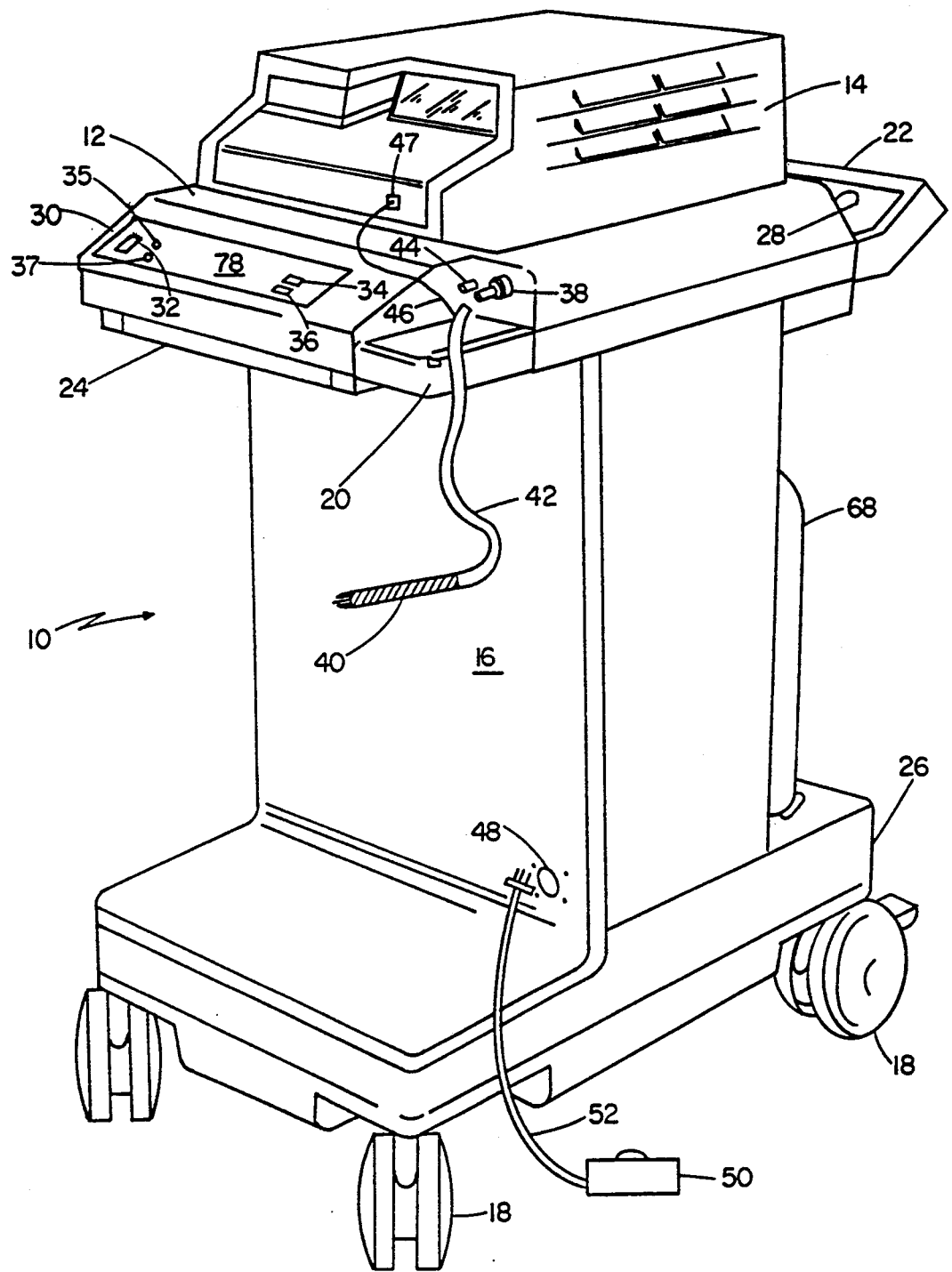
FIG. 1 is an isometric view of a cart constructed in accordance with one embodiment of the present invention.

Referring to FIG. 1, an electrosurgical cart constructed in accordance with one embodiment of the present invention is generally identified by the reference numeral 10. The cart 10 comprises an accessible platform 12 constructed and arranged to receive an electrosurgical generator 14. The generator 14 may comprise any electrosurgical generator currently manufactured, which may, due to the benefits of the cart 10, be used thereon in conjunction with an inert gas.

Fixed to the platform 12 is a support structure 16 which is provided with wheels 18 to facilitate the mobility thereof. The cart 10 is also provided with a front handle 20 and a rear handle 22 which allows an operator to easily push and/or pull the cart 10. Preferably, the rear handle 22 is angled upwardly with reference to horizontal to provide a convenient location for wrapping an external source power cord (not shown) while not in use.

A top drawer 24 may be provided for the storage of instruction manuals etc., and a lower drawer 26 may be provided for the storage of associated cables and controls. Conveniently located on a first end wall 28 of the platform 12 are controls and gauges for operation of the cart 10 and the generator 14, as will be subsequently described in greater detail. Similarly, located on a second end wall 30 of the platform 12 is a control panel 78 containing visual indications of, for example, a selected flow rate by an LED display 32, a low gas indicator light 34, an out of gas indicator light 36, an increase flow rate control button 35, and a decrease flow rate control button 37. Fixed to the panel 78 inside the platform 12 is a control logic panel 82, as will be subsequently described in greater detail. The lights 34 and 36 may also be combined with audible signals to assist an operator in rapid perception of the low or out-of-gas status.

Conveniently located on the platform 12 is a gas coupling 38 (which may be, for example, a panel mount gas quick coupling such as is available from Colder Products Co., St. Paul, Minn., under their part number LCD 160-04) for installing an electrosurgical pencil generally indicated by the reference numeral 40 (discussed in more detail below and illustrated in more detail in FIGS. 12, 13 and 14) by a gas tube 42. An electrical connection wire 46 exits the pencil 40 for connection to the electrosurgical generator 14 at an outlet 47 thereon. Although not shown, it is to be understood that a return pad must be used in conjunction with the generator 14 and the pencil 40 to complete a circuit formed between the generator 14, the pencil 40, and a patient.

Also conveniently located on the support structure 16 is a four-pronged outlet 48 for interconnection of a foot activated control 50, which is one alternative for controlling the provision of inert gas and current to the pencil 40 (other alternatives are discussed below). The foot control 50 may comprise, for example, a single pedal foot switch such as is available from Linemaster Switch Corp. of Woodstock, Conn., under their number 591-EX. The foot activated control 50 is removably attached to the outlet 48 by a power cable 52. Although not shown, it is to be understood that the foot control 50 may be an infrared transmitter coupled to the structure 16 by an infrared receiver therein without the need of a power cable 52 which may provide greater operating room freedom.

The platform 12 may be opened about a hinge 45 (FIG. 2) along the first end wall 28. The platform 12 must be secured from accidental opening thereof about the hinge by an appropriate latch device (not shown) which may be located proximate the second end wall 30. Also, slides 59 (FIG. 3) may be provided to allow the platform 12 to slide horizontally forward by pulling on the handle 20 or by pushing on the handle 22. By sliding the platform 12 forward, inert gas tanks 66 and 68 (FIGS. 2 and 4) may be changed with greater ease than if the platform 12 did not slide. Appropriate slide locks (not shown) will be provided to prevent accidental sliding of the platform 12.

Figure 2:
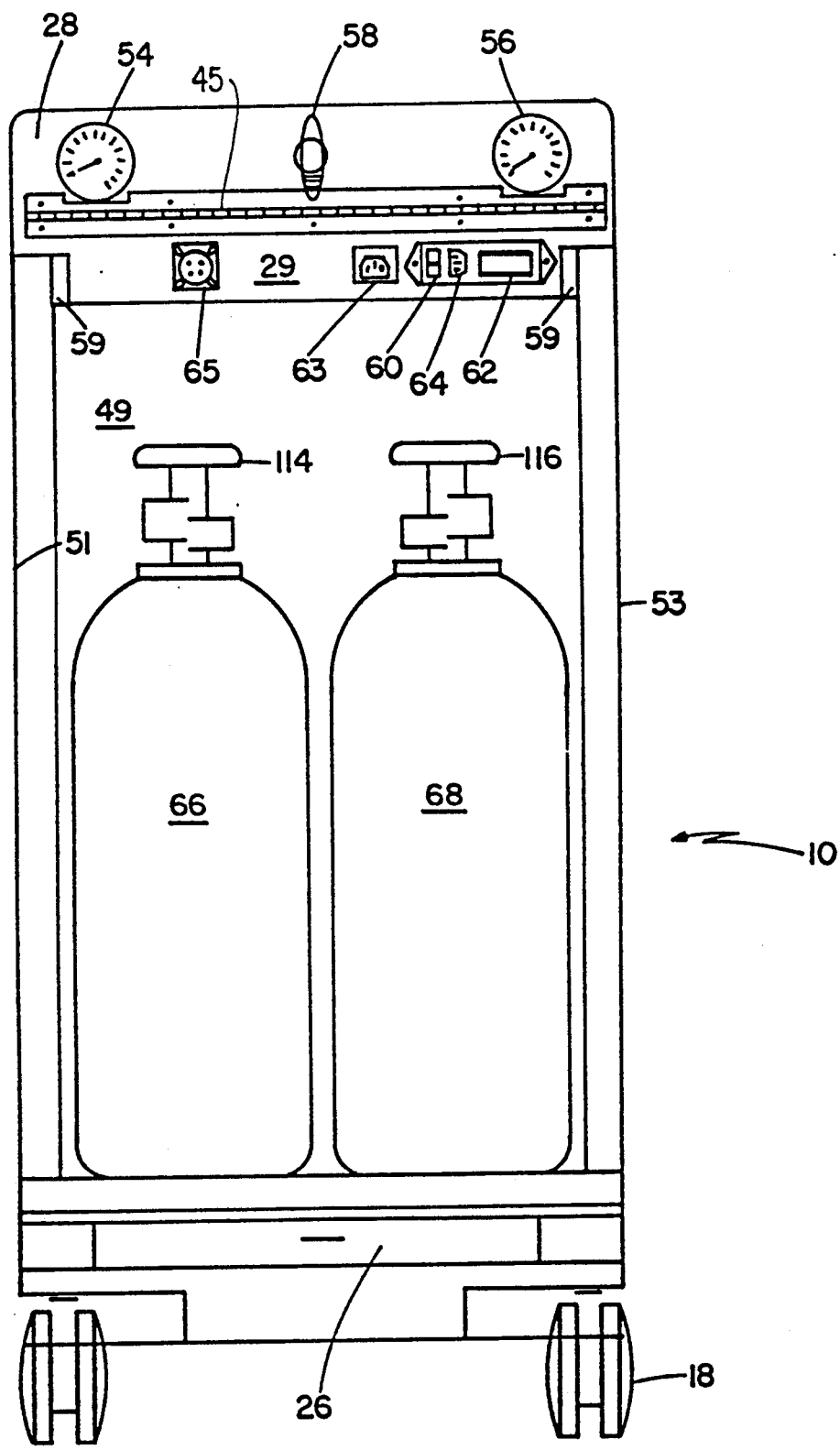
FIG. 2 is a rear elevation of the cart of FIG. 1.

Referring to FIG. 2, a rear elevation of the cart 10 is shown revealing that the structure 16 comprises a three-sided container with a front wall 49, first and second side walls 51 and 53, and an open back. Located within the first end wall 28 of the platform 12 is a first pressure gauge 54 and a second pressure gauge 56. The gauges 54 and 56 may comprise, for example, two inch gauges registering 0-3000 psi such as are available from McDaniel Controls, Inc. of Luling, La., under their part number TNU, and are provided to allow an operator or an assistant to the operator (such as a nurse) to monitor the pressure within the inert gas tanks 66–68 in order to choose the appropriate tank for surgical use. A three-way valve 58 is also conveniently located on the wall 28 to allow selection of the inert gas tank 66 or 68. Depending from the gauges 54, 56 and the valve 58 are appropriate hoses and connectors (FIG. 4) for attachment to the tanks 66 and 68, as will be subsequently described in greater detail.

Figure 4:
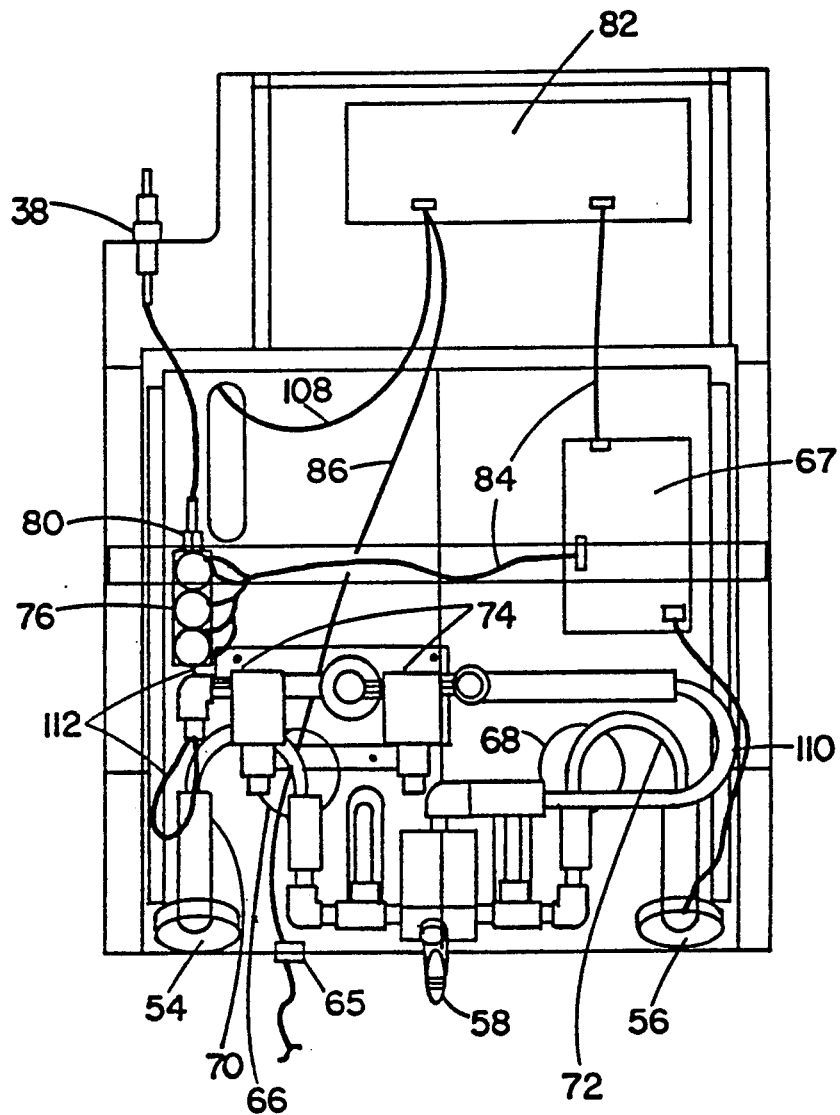
FIG. 4 is a top plan view of the cart of FIG. 1 with the top surface removed.

Also located on a panel 29 below the first end wall 28 is a power switch 60 and a power selector 62. An external power source (not shown) may be plugged into the power selector 62 via an electrical inlet 64 which may comprise an improved three prong International Electric Code (IEC) socket. The power selector 62 may comprise, for example, a power entry module capable of selectively receiving 100, 120, 220 or 240 volts of alternating current (VAC), such as is available from Corcom, Inc. of Libertyville, Ill. under their part number 6 Vm4S. A power supply 67 is provided to convert any of the incoming VAC's from the power selector 62 to twelve volts of direct current (VDC). The power supply 67 may be, for example, a power supply such as is available from Condor, Inc. of Oxnard, Calif. under their model number HC12-3.4-A. The twelve VDC is required by the control logic panel 82 and a flow control valve assembly 76 (FIG. 4). The power switch 60 provides the capability through, for example, a toggle switch, to turn the power to the entire cart 10 on or off.

Adjacent the power switch 60 is a power outlet 63, which may comprise a standard three prong IEC socket, for providing the electrical power to the generator 14. Also on the panel 29 is a four prong outlet 65 which is used in conjunction with a power cable and an inlet (neither shown) on the generator 14. The outlet 65 allows a convenient and orderly interconnection between the foot activated control 50 and the generator 14. By interconnecting the generator 14 and the control 50 through the outlet 65, an operator is afforded the benefits of the simultaneous control of electrical output and inert gas to the pencil 40.

Figure 12:
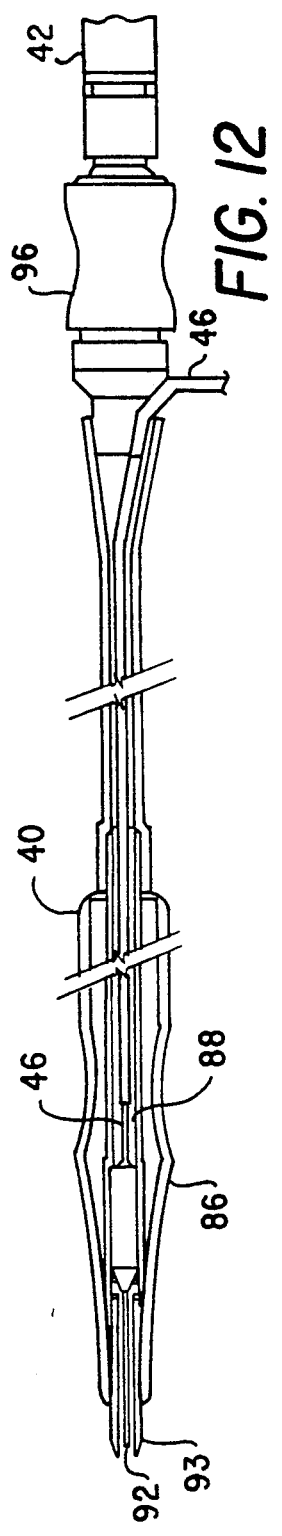
FIG. 12 is a cross-sectional view of one embodiment of an electrosurgical pencil usable with the present invention.

Referring to FIG. 12, a more detailed illustration of the electrosurgical pencil 40 for use with the cart 10 is shown. The pencil 40 comprises a plastic case 86 of an insulating material. Within the hollow passageway 88 of the case 86 is the electrical wire 46 through which electricity passes to a tungsten electrode 92. A ceramic tip 93 in the general shape of a hollow frustum surrounds the electrode 92 and serves to help direct the inert gas therearound. A flexible gas tube 42 is connected at one end to a connector 96 positioned on one end of the pencil 40. The tube 42 is then connected at a second end 98 (see FIG. 1) to the coupling 38 on the platform 12. The wire 46 exits the pencil 40 at the connector 96 or at the second end 98 for interconnection to the electrosurgical generator 14 through the outlet 47 thereon. Thus, electricity is allowed to flow from the generator 14 through the wire 46 and to the electrode 92. Simultaneously, inert gas flows through the gas tube 42 to surround the wire 46 and the electrode 92. The electrode 92 ionizes the inert gas which enhances the function of the pencil 40 to coagulate the blood of a patient. The enhancement of electrosurgery with an inert gas has been shown to lower the amount of tissue desiccation over non-gas electrosurgery. Thus inert gas-enhanced electrosurgery provides a technique allowing surgeons to obtain more blood coagulation with less tissue desiccation and less blood loss.

Figure 3:
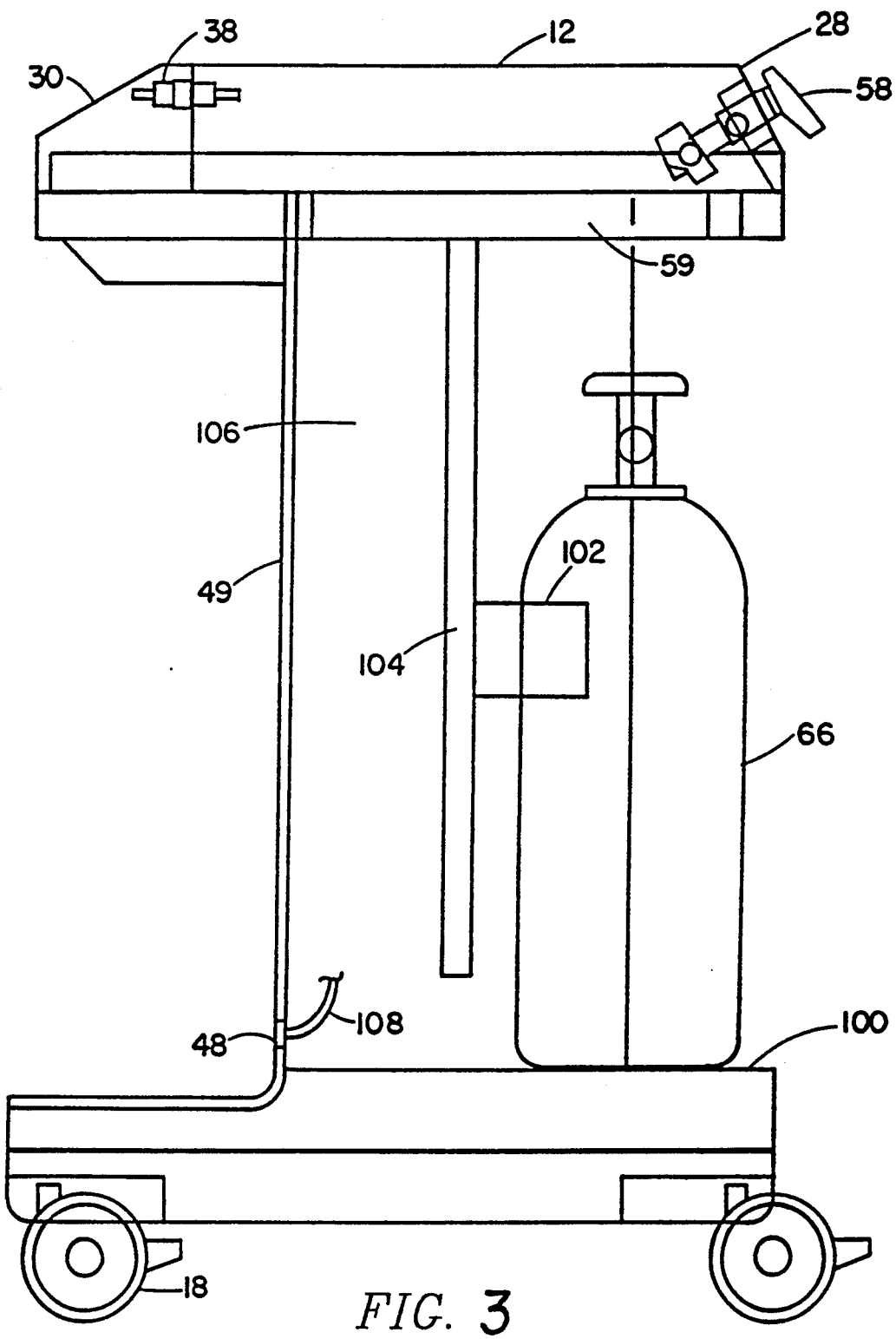
FIG. 3 is a side view of the cart of FIG. 1.

Referring to FIG. 3, a side view of the cart 10 is shown with the first side wall 51 removed for clarity. Preferably, located within the cart 10 and fixed to the platform 12 are the various controls and interconnections (FIG. 4) required to operate the electrosurgical generator 14 and the pencil 40. Conveniently located toward the rear of the cart 10 are the first and second gas tanks 66 and 68 which may contain an inert gas, preferably argon.

The tanks 66, 68 sit within depressions formed in a base plate 100 of the cart 10. The tanks 66, 68 are held in place by support brackets 102 which are fixed to a middle wall 104. The wall 104 is connected on each end thereof to the first and second side walls 51, 53 to provide lateral support to the cart 10. Between the front wall 49 and the middle wall 104 is a cavity 106 within which runs a power interconnect cable 108. The cable 108 connects the outlet 48 for the foot control 50 through the control logic panel 82 (FIG. 4) to the four prong outlet 65 (FIG. 2).

Referring to FIG. 4, a detailed top plan view of the platform 12 is shown with a top surface thereof removed for the sake of clarity. The pressure gauges 54, 56 are connected to the gas tanks 66, 68 by gas hoses 70 and 72, respectively. The hoses 70, 72 also connect the tanks 66, 68 to the three-way valve 58. A hose 110 connects the three-way valve 58 into a two stage regulator 74 which may comprise, for example, a brass regulator such as is available from Victor Equipment Company of Denton, Tex. under their part number TBD. The regulator 74 provides a pressure drop in a first stage thereof from the tanks 66, 68 (which are approximately 2400 PSI) to 100 PSI. A second stage of the regulator 74 further drops the pressure from 100 PSI to 30 PSI which is appropriate for use with the generator 14 and the pencil 40. Although not shown, sensors may be positioned around the regulator 74 to signal the low gas indicator 34 and the out of gas indicator 36 on the control panel 78.

Interconnected to the regulator 74 through a hose 112 is a flow control valve assembly 76. The flow control valve assembly 76 may comprise, for example, three solenoid valves such as are available from Automated Systems Product of Simi Valley, Calif. under their part number 63-211-N103-20, which allow a gas flow rate of 4, 6, 8, 10 or 12 liters per minute. The flow rate is selectable from the buttons 35 and 37 located on the control panel 78.

An outlet 80 on the flow control valve assembly 76 directs the selected flow rate of gas to the coupling 38 and thence to the pencil 40. The flow control valve assembly 76 is interconnected to the control logic panel 82 via electrical wires 84 through the power supply 67. The control logic panel 82 may comprise, for example, an arrangement of printed circuit boards capable of coordinating a release of the flow of gas and electricity by a signal from the foot control 50. The electrosurgical generator 14 is interconnected to the control logic panel 82 and thus the foot control 50 by a wire 86 and to the four prong outlet 65, as previously described.

In operation, the platform 12 would be slid forward along its provided slides 59 to allow insertion of the gas bottles 66 and 68. The gas lines 70 and 72 would be connected to the tanks 66, 68 and the gas would be allowed to flow therethrough by the opening of valves 114 and 116 (FIG. 2) which are integral with the tanks 66, 68. Gas would thus flow to the pressure gauges 54, 56 and would further be allowed to flow, based upon the positioning of the three-way valve 58, to the regulator 74 for the appropriate pressure drops.

From the regulator 74, gas would enter the flow control valve 76 assembly which would allow flow to the coupling 38 based upon the selected flow rate upon receipt of a signal from the foot control 50. Electrical power would be provided to the cart 10 through the electrical inlet 64. The power switch 60 allows electricity to be available upon need. Upon activation of the foot control 50 by a surgeon, electrical output and inert gas would flow to the electrosurgical pencil 40 for use in surgery to coagulate blood.

Figure 5:
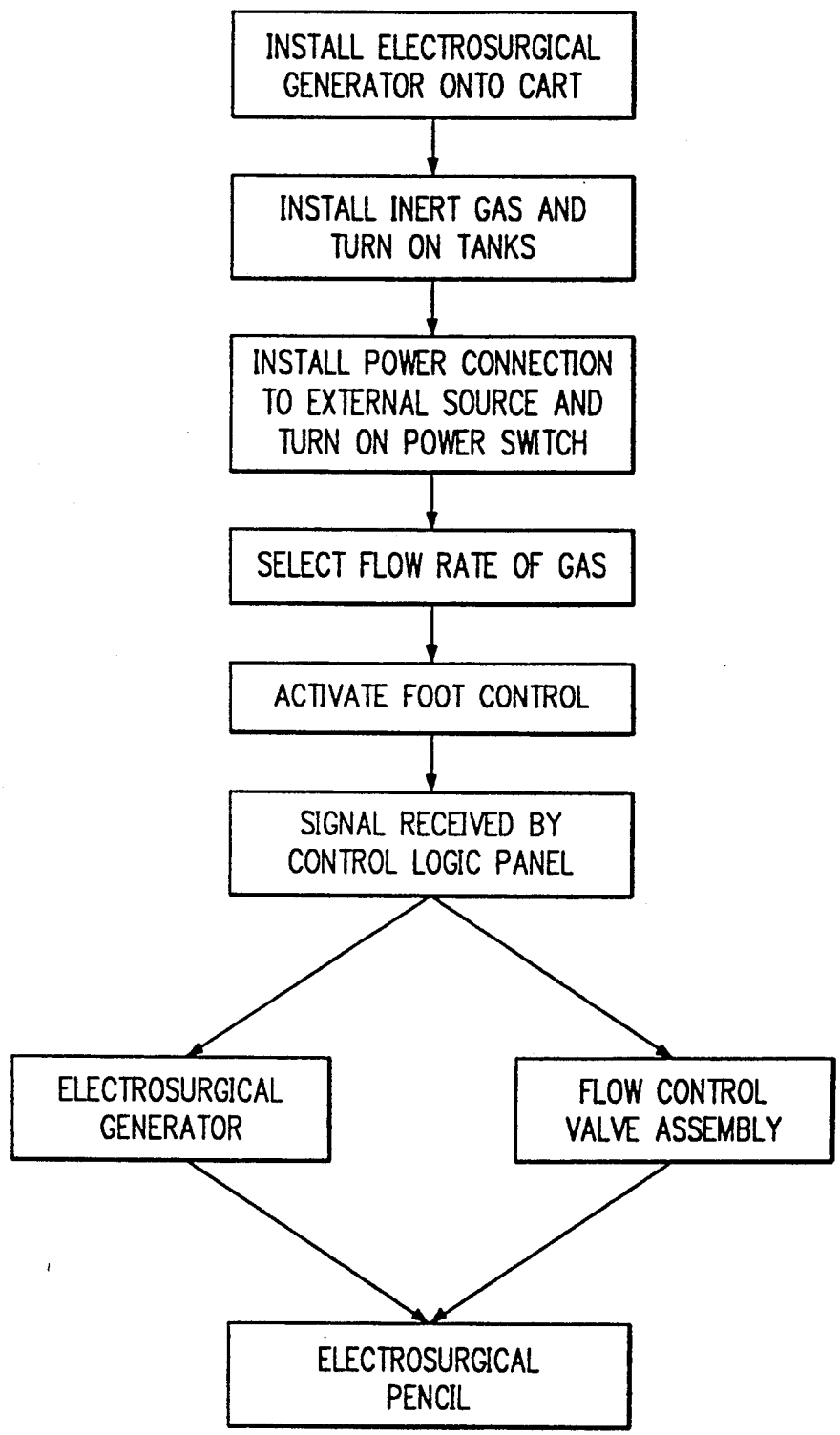
FIG. 5 is a flow chart of the operation of the cart of FIG. 1.

Referring to FIG. 5, a flow chart schematically showing the operation of the cart 10 is illustrated. The first step in the operation of the cart 10 is, of course, to install any electrosurgical generator onto the platform 12 of the cart 10. The inert gas tanks 66, 68 are installed onto the cart 10 and the integral valves 114 and 116 thereon opened to activate flow of the gas. A power cord is plugged into the electrical inlet 64 and an external power source, followed by turning on the power switch 60. An operator then selects the desired gas flow rate by depressing the control buttons 35 and/or 37 on the control panel 78. The operator activates the foot control 50 which sends a signal to the control logic panel 82 which simultaneously signals the electrosurgical generator 14 (to start the flow of electricity) and the flow control valve assembly 76 (to start the flow of inert gas). The operator may then perform the desired surgical procedure on a patient. By monitoring the control panel 78 and the pressure gauges 66, 68, the cart 10 may be operated efficiently for inert gas enhanced electrosurgery.

Figure 6:
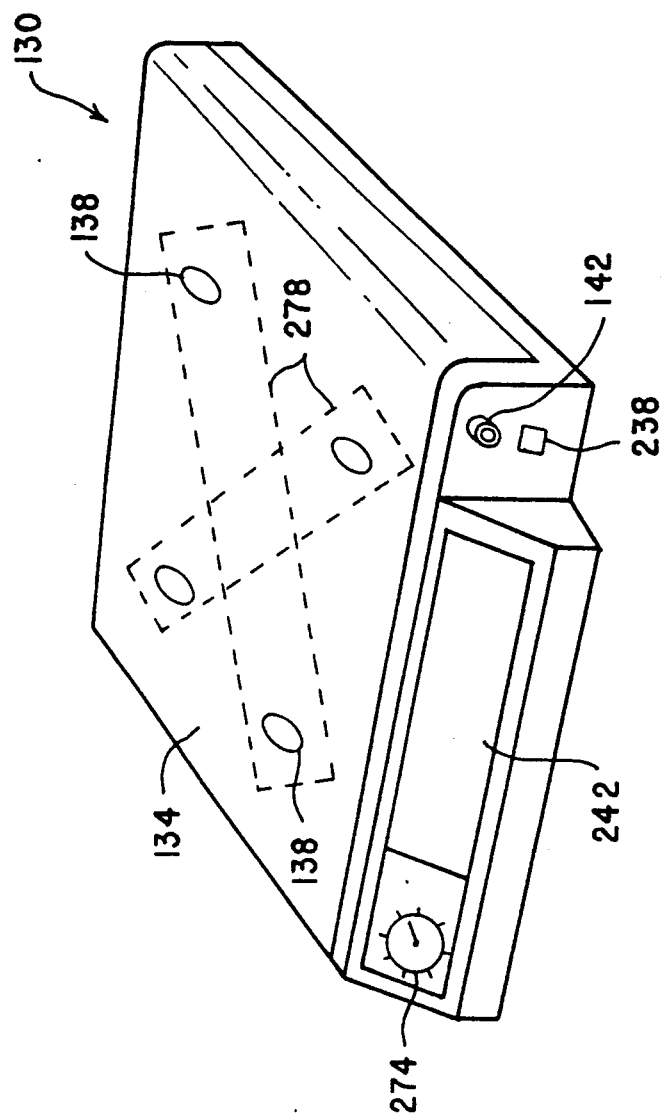
FIG. 6 is an isometric view of a portable unit constructed in accordance with another embodiment of the present invention.

Another embodiment of the present invention is illustrated in FIGS. 6-11. Referring first to FIG. 6, a portable unit constructed in accordance with another embodiment of the present invention is generally identified by the reference numeral 130. The portable unit 130 can be used on table tops, counters, surgical carts or any other appropriate surface. The portable unit 130 functions in part to receive and support an electrosurgical generator (such as the generator 14 shown in FIG. 1) and thus includes an accessible platform 134. In order to stabilize and locate the electrosurgical generator on the platform 134, a plurality of recessed receivers 138, arranged to coincide with legs which commonly extend from the generator, are provided on the surface of the platform 134. Support brackets 278 are also provided to enhance the structural integrity of the portable unit 130.

Figure 7:
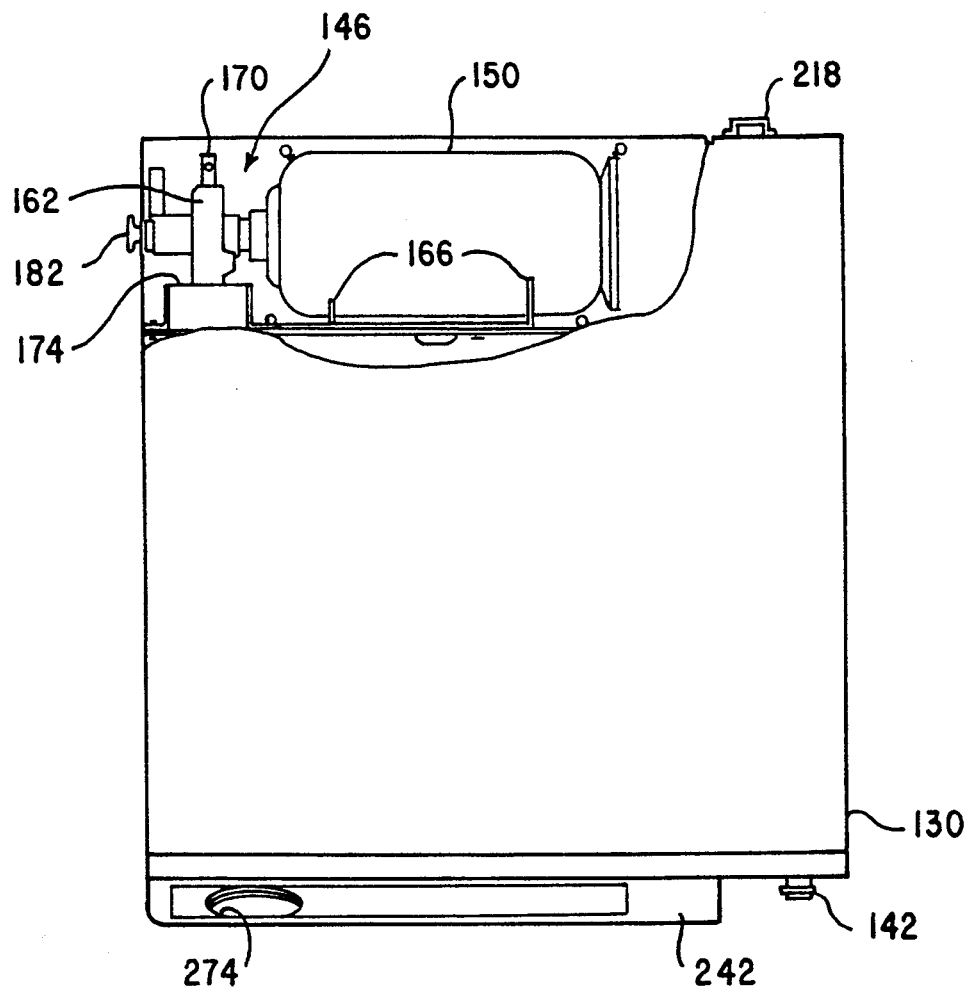
FIG. 7 is top plan view of the portable unit of FIG. 6 with a portion of the top surface removed.
Figure 8:
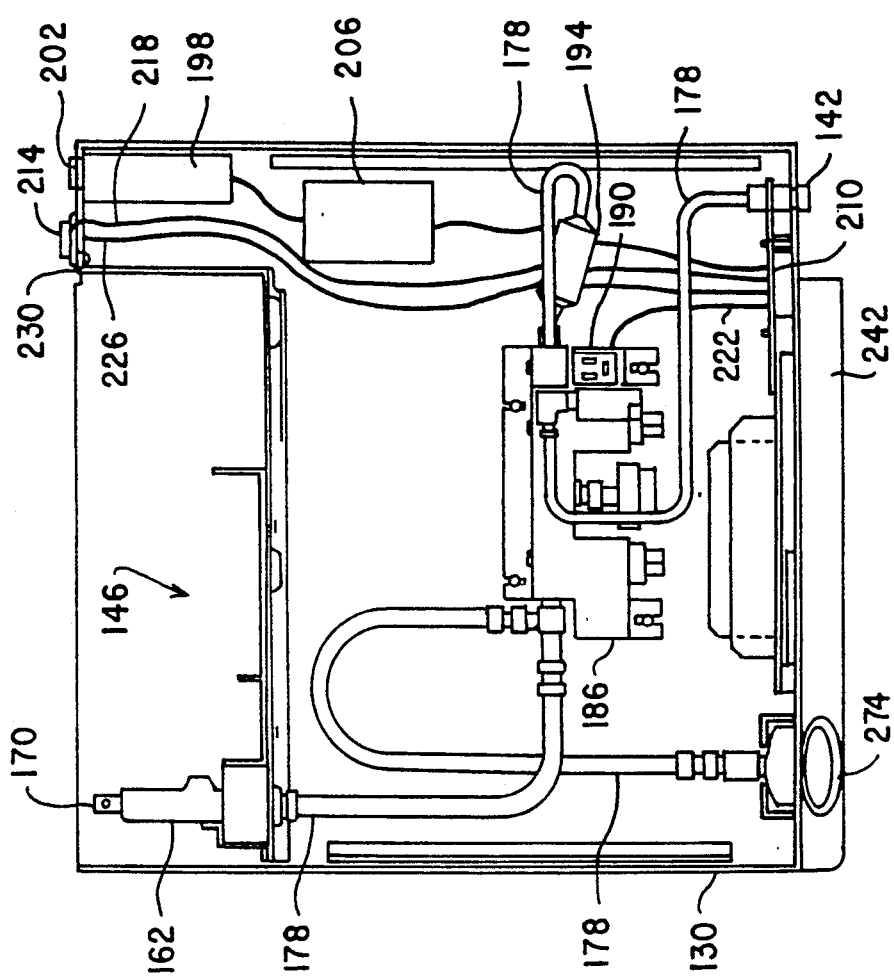
FIG. 8 is a top plan view of the portable unit of FIG. 6 with the entire top surface removed.
Figure 9:
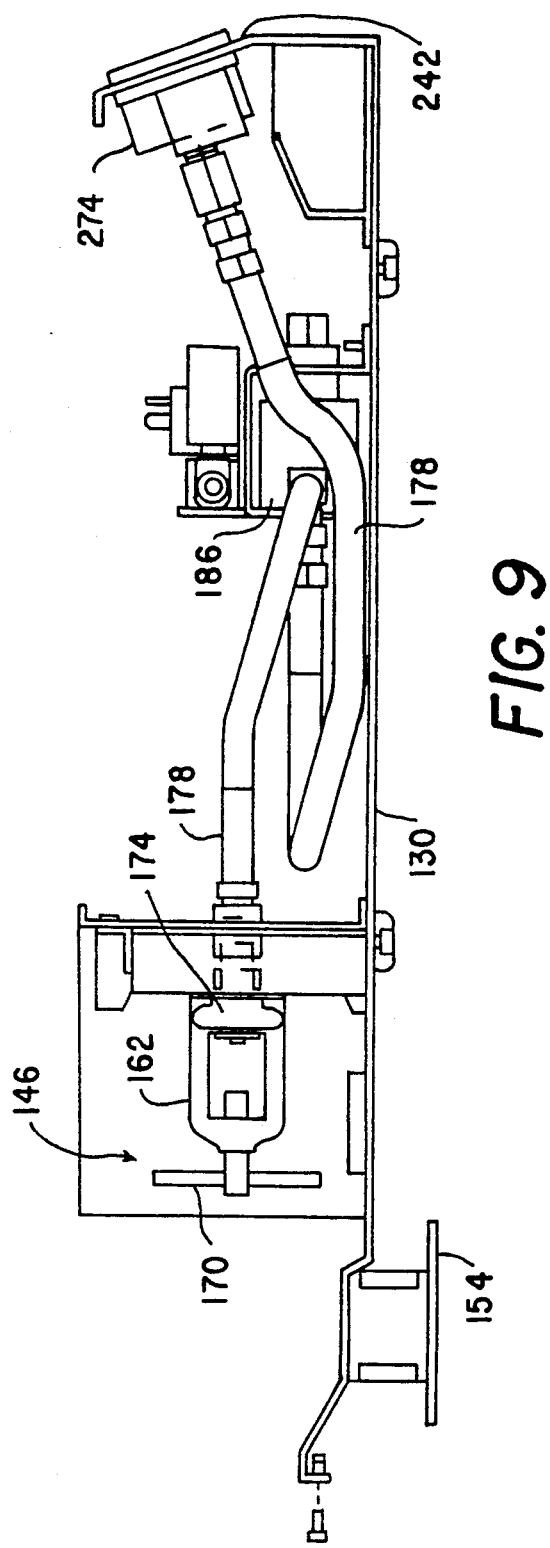
FIG. 9 is a side view of the portable unit of FIG. 6 with the side panel removed and the rear access door in an open position.
Figure 10:
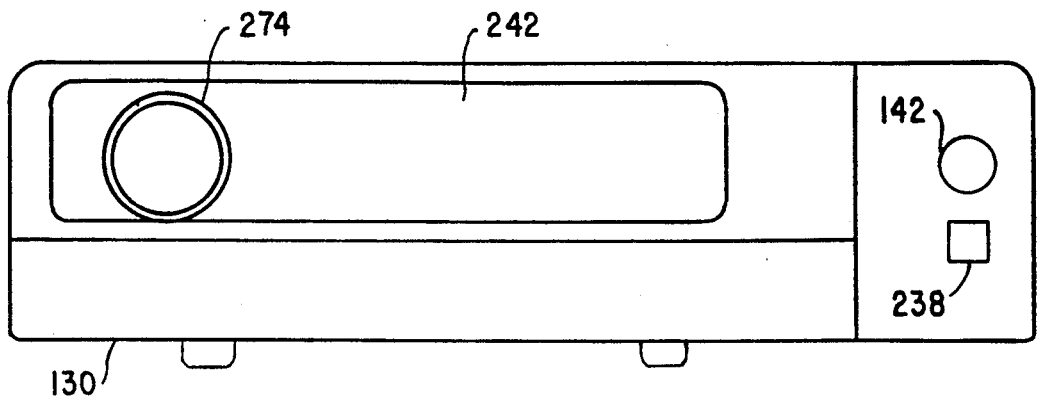
FIG. 10 is a front elevation of the portable unit of FIG. 6.
Figure 13:
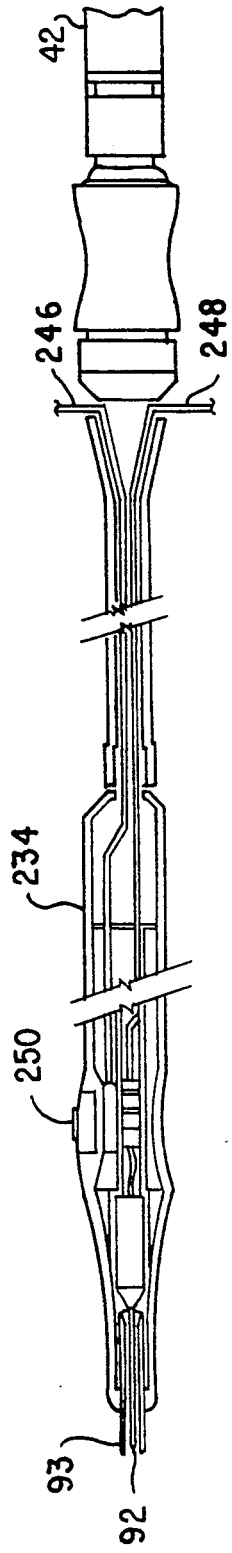
FIG. 13 is a cross-sectional view of a second embodiment of an electrosurgical pencil usable with the present invention.
Figure 14:
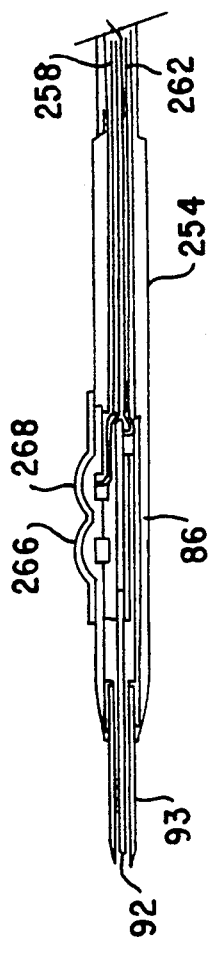
FIG. 14 is a cross-sectional view of a third embodiment of an electrosurgical pencil usable with the present invention.

In addition to supporting the generator, the portable unit 130 functions as an interface between the generator, an electrosurgical pencil (various embodiments of which are illustrated in FIGS. 12-14 and discussed in more detail below), and a supply of inert gas so that gas-enhanced electrosurgery is achievable. In this regard, the portable unit 130 includes a gas coupling 142 as illustrated in FIG. 6, similar to gas coupling 38 described above with regard to the cart 10, which is designed to receive, typically through interconnecting devices, electrosurgical pencils of the types illustrated in FIGS. 12-14. Moreover, as illustrated in FIGS. 7-9, the portable unit 130 also has a tank receiving area 146 in which a storage tank 150 (FIG. 7), which contains a supply of an appropriate inert gas, may be positioned.

Figure 11:
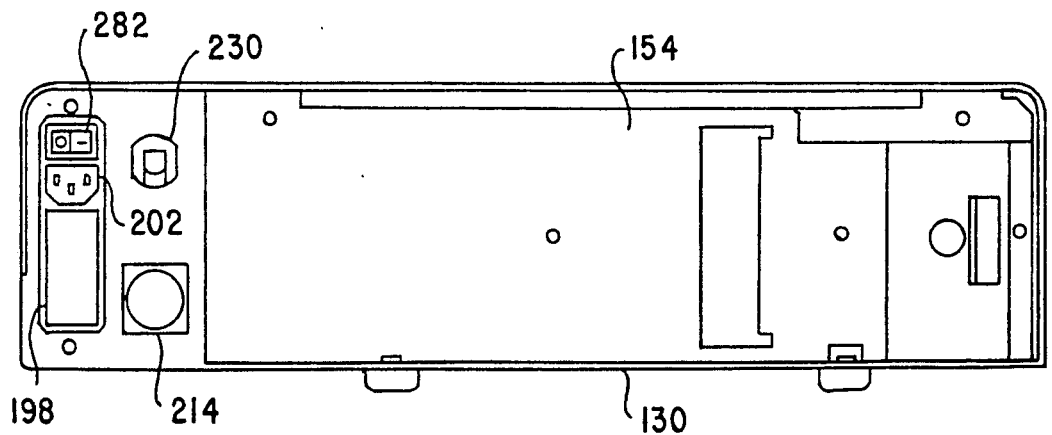
FIG. 11 is a rear elevation of the portable unit of FIG. 6.

In order to allow the portable unit 130 to be easily transported between locations, it may be desirable to impose certain size limitations on its physical structure. However, the portable unit 130 is designed to accommodate for such size limitations and still provide the desired functions of the present invention. For instance, the receiving area 146 in the rear portion of the portable unit 130 is designed such that the storage tank 150 may be horizontally positioned therein as best illustrated in FIG. 7. The storage tank 150 may be easily positioned within this receiving area 146 by opening a rear access door 154 (FIG. 9) positioned on the rear panel 158 of the portable unit 130 (FIG. 11). When properly positioned in the receiving area 146, the storage tank 150 may be secured therewithin by placing a neck portion of the storage tank 150 through a yoke 162 and by positioning a body portion of the storage tank 150 against metal brackets 166.

The storage tank 150 is fluidly interconnected with the gas coupling 142 which receives an electrosurgical pencil, various types of which are illustrated in FIGS. 12-14. The portable unit 130 of the present invention includes a number of features directed to this desired connection. By engaging the clamping assembly 170 positioned in the yoke 162, best illustrated in FIG. 9, a fluid connection is established between the storage tank 150, via an adapter assembly on its neck portion (not shown), and an adaptor 174 which is connected to a conduit 178 through which inert gas may flow from the storage tank 150, ultimately to the gas coupling 142. In order to actually initiate this fluid connection, a tank valve 182, connected to the storage tank 150, is positioned exterior of the physical structure of the portable unit 130 for the convenience of the operator.

As was the case with the tanks 66 and 68 of the cart 10 of FIGS. 1-4, the pressure of the inert gas within the storage tank 150 is much higher than is desired for use in electrosurgery. Consequently, the portable unit 130 includes a regulator 186, connected within the conduit 178, which may utilize multiple stages to provide the desired pressure drop. For instance, the regulator 186 may be a two stage device as discussed above such that the first stage will reduce the flow received from the storage tank 150 to approximately 140 PSI, while the second stage will reduce the pressure to approximately 23 PSI.

In order to allow the operator to control the provision of inert gas to the electrosurgical pencil, a solenoid valve 190, having a particular orifice size therein, may also be interconnected to the conduit 178. The solenoid valve 190 has an orifice therein of a given size through which the inert gas may flow, and may be selected, based upon the size of the orifice, to provide the desired flow rate to the electrosurgical pencil. The solenoid valve 190 is effectively connected to the particular operator control mechanism being used with the portable unit 130 (discussed in more detail below), and thus can be activated to either allow or prevent the flow of the inert gas to the gas coupling 142 and thus to the particular electrosurgical pencil attached thereto by effectively opening and closing the orifice. As can be appreciated, the solenoid valve 190 may be detachably connected to allow replacement with another solenoid valve (not shown) having a different sized orifice to alter the flow rate provided to the electrosurgical pencil. Moreover, a configuration such as that described above with regard to the cart 10 may be utilized such that a multiple port control valve assembly (i.e., having a plurality of orifices of different cross-sectional areas) may be used with solenoids such that an operator can choose between various flow rates. When using a multiple port valve, flow rate control buttons as previously described above will be provided on the unit 130. In order to reduce the potential for foreign materials becoming lodged in the solenoid valve 190 and/or being propelled against a patient undergoing surgery, it may be desirable to utilize a filter 190 to remove foreign materials from the flow of inert gas prior to entering the solenoid valve 190.

In operation, the storage tank 150 is positioned in the receiving area 146 of the portable unit 130 and is fluidly connected to the adaptor 174. Once the tank valve 182 is opened, inert gas flows through the conduit 178 to the regulator 186 where the desired pressure drop is achieved. The inert gas then passes through a filter 194 and to the solenoid valve 190. When the operator activates the particular operator control mechanism being used (discussed below), inert gas flows through the solenoid valve 190 and the conduit 178 to the gas coupling 142, and thus to the particular electrosurgical pencil attached thereto.

The portable unit 130 also allows for the interface of a supply of inert gas with an electrical output provided to the pencil by an electrosurgical generator. The present invention includes a number of features to accommodate this interface. Initially, referring to FIG. 11, the portable unit 130 includes a power selector 198 positioned on the rear panel 158 which can receive power from an external power source (not shown) via an electrical inlet 202 also positioned on the rear panel 158. As in the case of the cart 10 of FIGS. 1-4, the power selector 198 may comprise, for example, a power entry module capable of selectively receiving 100, 120, 220 or 240 volts of VAC. A power switch 282 is provided to control the provision of electricity to the portable unit 130. The inlet 202 may be of the type discussed above, namely an improved three prong IEC socket. A power supply 206 is again provided to convert any of the incoming VAC's from the power selector 198 to twelve volts of direct current. As opposed to the cart 10 described above, a generator placed on the portable unit 130 can be directly connected to an external power supply (such as a wall outlet) rather than through the unit 130.

The power supply 206 supplies power in part to the control logic panel 210, similarly as with the control logic panel 82 discussed above with regard to the cart 10, as best illustrated in FIG. 8. The control logic panel 210 receives an appropriate signal(s) from the operator control device being used (discussed below), and sends a signal(s) to initiate the provision of inert gas and/or electrical output to the particular electrosurgical pencil. As previously stated an electrosurgical pencil as illustrated in FIGS. 12-14 will be interconnected with the gas coupling 142 by an appropriate flexible tube, such as the gas tube 42 illustrated in FIG. 1. Depending upon the particular operator control device being used, the portable unit 130 will function to provide the desired interface in a variety of ways.

The portable unit 130 may be used with the foot activated control 50 of FIG. 1, which again controls the provision of both inert gas and electrical output to the type of electrosurgical pencil 40 illustrated in FIGS. 1 and 12. In order to accommodate the use of this particular operator control mechanism, the portable unit 130 includes a foot plug 214 positioned on the rear panel 158, as illustrated in FIG. 11, to receive the power cable 52 connected to the control 50 (FIG. 1). This foot plug 214 is electrically connected to the logic control panel 210 by a foot plug wire 218 such that when foot control 50 is activated by an operator, the logic control panel 210 sends a signal through a solenoid wire 222 to the solenoid valve 190 to open the orifice therein such that inert gas begins flowing to the electrosurgical pencil, of the type illustrated in FIG. 12, which is appropriately attached to the gas coupling 142 as described above. Furthermore, the control logic panel 210 sends a signal through the generator wire 226 to a generator pigtail outlet 230, positioned on the rear panel 158 such that when the electrosurgical generator is connected thereto by an appropriate cable (not shown), the generator will provide the desired electrical output to the electrosurgical pencil 40 (FIG. 12) as described above with regard to the cart 10.

In some instances, it may be desirable to have the operator control mechanism incorporated within the structure of the electrosurgical pencil to provide more convenient access thereto by the operator, such as with the electrosurgical pencil 234 illustrated in FIG. 13. The portable unit 130 of the present invention also incorporates features to accommodate for use of this particular combination control mechanism/surgical device. For instance, a jack 238 (see FIG. 6) is provided on a front panel 242 of the portable unit 130, which is electrically connected to the control logic panel 210. A wire 246 from the pencil 234 is then positioned in this jack 238. Consequently, when a switch 250 on the electrosurgical pencil 234 is depressed, an appropriate signal is sent to the control logic panel 210 through the wire 246. The control logic panel 210 then sends an appropriate signal to the solenoid valve 190 via the solenoid wire 222 to initiate the flow of inert gas to the pencil 234. The control logic panel 210 also simultaneously sends an appropriate signal to the electrosurgical generator via the generator wire 226, the generator pigtail outlet 230 electrically connected thereto, and the connecting cable (not shown) to initiate the flow of electrical output to the pencil 234 as described above, such as through a wire 248 which is connected to the outlet 47 on the generator 14 (FIG. 1). As can be appreciated, the cart 10 of FIGS. 1-4 may also be structurally modified to also accommodate the use of the electrosurgical pencil 234.

In some instances, it may not only be desirable to have a hand versus foot control for the electrosurgical pencil, but it also may be desirable to allow an operator to independently control the provision of inert gas and electrical output to the electrosurgical pencil. An electrosurgical pencil 254 providing these functions is illustrated in FIG. 14 and the present invention includes features to accommodate for the use thereof. For a more complete description of the pencil 254, refer to U.S. patent Ser. No. 495,449 to Fleenor, filed Mar. 16, 1990, which is incorporated herein by reference. The electrosurgical pencil 254 has a first wire 258 and a second wire 262. The first wire 258 may be connected to the jack 238 (see FIG. 6) on the front panel 242 of the portable unit 130 to send a signal to the control logic panel 210 to initiate the flow of inert gas in the manner described above when the appropriate control is activated by the operator (discussed below). However, instead of using the control logic panel 210 to initiate the provision of electrical output to the electrosurgical pencil 254, the second wire 262 is directly connected to the electrosurgical generator 14 via the outlet 47 (FIG. 1) to send a signal thereto and electrical output is then provided to the pencil 252 through wire 262, in a manner as discussed above, when activated by the operator (discussed below).

The first and second switches 266, 268 of the pencil 254 may be configured to allow the operator the desired control over the provision of inert gas and electrical output. For instance, the first switch 266 may be connected such that when activated, a signal will be sent to the generator to ultimately provide electrical output to the pencil 254 at a first level. The second switch 268 may then be a two-stage switch such that when activated at the first stage, a second signal is sent to the generator to provide a second level of electrical output to the pencil 254. When the second stage is activated, a signal may also be sent to the control logic panel 210 to initiate the flow of inert gas to the pencil 254. As can be appreciated, the cart 10 of FIGS. 1–4 may also be modified in order to accommodate the use of this pencil 254 and its control features.

Based upon the foregoing description, those skilled in the art will appreciate that the portable unit 130 of the present invention is versatile in having components which allow for the use thereof with a wide variety of operator control devices. However, the portable unit 130 also provides the operator with features which will be of assistance when performing gas-enhanced electrosurgery. For instance, as with the cart 10 of FIGS. 1–4, operating monitors such as low gas indicator lights (not shown) may be connected to a pressure switch 286 which is positioned between, for instance, the first and second stages of the regulator 186. Consequently, when the pressure from the first stage is approximately 85 PSI, the low gas indicator light will be activated to indicate to the operator that only a limited quantity of inert gas remains for performing gas-enhanced electrosurgery. Moreover, out-of-gas indicator lights (not shown), low gas level alarms (not shown), flow rate indicators, and a pressure gauge 274 appropriately incorporated within the conduit 178 (FIGS. 8–9) may also be incorporated within the portable unit 130 to assist in monitoring operations.

Although not shown, it is to be understood that electrical interconnection of the generator to the cart 10 or the unit 130 may not be required for use of the pencil 40 or the pencil 234. It is possible to send the electrical output from the generator through the control logic panels. The control logic panels would then signal the initiation of inert gas and provide the pencil's electrode with electrical energy.

Although the present invention has been described with respect to specific embodiments thereof, various changes and modifications may be suggested to one skilled in the art, and it is intended that the present invention encompass such changes and modifications as fall within the scope of the appended claims.

What is claimed is:

1. An apparatus for supporting and operatively interfacing one of a plurality of standard electrosurgical generators provided with a selected standard electrical plug, an electrosurgical pencil, and at least one gas receptacle to permit an operator to conduct gas-enhanced electrosurgery, comprising:
   a support structure having an accessible platform for receiving and removably supporting said one of said plurality of standard electrosurgical generators;
   first receiving means, mounted on said support structure, and adapted for receiving the at least one gas receptacle;
   second receiving means, mounted on said support structure, adapted for receiving the electrosurgical pencil and interconnected to said first receiving means;
   control interface means, mounted on said support structure, interconnected to said first receiving means and connectable to operator control means, wherein an operator may control with said operator control means the provision of gas from the at least one gas receptacle to the electrosurgical pencil and the provision of an electrical output from said one of said plurality of standard electrosurgical generators to the electrosurgical pencil to conduct gas-enhanced electrosurgery; and
   accessible outlet means, mounted on said support structure and adapted for connectably receiving said selected standard electrical plug, said outlet means selectively interconnected said one of said plurality of standard electrosurgical generators to said control interface means.

2. An apparatus, as claimed in claim 1, wherein said support structure is portable.

3. An apparatus, as claimed in claim 1, wherein said first receiving means is substantially contained within said support structure.

4. An apparatus, as claimed in claim 1, wherein said first receiving means comprises:
   a regulator for controlling the pressure of the inert gas provided to the electrosurgical pencil;
   a valve for controlling the flow rate of the inert gas provided to the electrosurgical pencil; and
   means for connecting the at least one gas receptacle to said regulator, said regulator to said valve, and said valve to second receiving means.

5. An apparatus, as claimed in claim 4, wherein said valve is detachably connected between said regulator and said second receiving means.

6. An apparatus, as claimed in claim 1, wherein said control interface means comprises a control logic panel.

7. An apparatus, as claimed in claim 1, wherein said control interface means is interconnected with said standard electrosurgical generator.

8. An apparatus, as claimed in claim 1, wherein said operator control means comprises a foot-activated switch.

9. An apparatus, as claimed in claim 8, wherein said foot-activated switch is operatively interconnected to said support structure by cable means.

10. An apparatus, as claimed in claim 8, wherein said foot-activated switch is operatively interconnected to said support structure by infrared means.

11. An apparatus, as claimed in claim 1, wherein said operator control means comprises at least one selectable switch positioned on the electrosurgical pencil.

12. An apparatus, as claimed in claim 1, wherein said operator control means comprises first and second selectable switches positioned on the electrosurgical pencil.

13. An apparatus, as claimed in claim 12, wherein activation of said first switch provides an electrical output to the electrosurgical pencil at a first level, and wherein said second switch is two-stage, activation of said first stage providing an electrical output to said electrosurgical pencil at a second level and activation of said second stage providing inert gas to the electrosurgical pencil.

14. An apparatus, as claimed in claim 1, further comprising flow rate indicator means interconnected to said first receiving means, wherein a flow rate of the inert gas provided to the electrosurgical pencil is indicated to an operator.

15. An apparatus, as claimed in claim 1, further comprising indicator means interconnected to said first receiving means, wherein an indication is provided to an operator when an amount of inert gas in the at least one inert gas receptacle drops below a predetermined value.

16. An apparatus, as claimed in claim 1, further comprising pressure indicating means interconnected to said first receiving means, wherein an internal pressure of the at least one inert gas receptacle is indicated to an operator.

17. An apparatus, as claimed in claim 1, wherein said outlet means is operative for transmission of an interface signal to coordinate said provision of gas and electrical output to the electrosurgical pencil to conduct gas-enhanced electrosurgery.

18. An apparatus, as claimed in claim 1, further comprising second outlet means connectable to an external power source.

19. An apparatus, as claimed in claim 18, wherein said second outlet means is interconnected to said control interface means to provide power thereto.

20. An apparatus, as claimed in claim 19, further comprising means interconnected between said second outlet means and said control interface means for converting an alternating current received from said external power source to a direct current.

21. An interfacing and supporting apparatus for one of a plurality of standard electrosurgical generators provided with a selected standard electrical plug, an electrosurgical pencil and a gas receptacle to permit an operator to conduct gas-enhanced electrosurgery, comprising:

a support structure having an accessible platform for receiving and removably supporting the said one of said plurality of standard electrosurgical generators;

first receiving means mounted to said support structure for receiving and fluidly engaging the gas receptacle;

adaptor means mounted on said support structure for fluidly engaging the electrosurgical pencil;

manifold means, including control valve means, for interconnecting said first receiving means and said adaptor means, wherein gas flows from the receptacle to the pencil;

operator control receiving means connected to said support structure for receiving operator control means, said operator control receiving means interconnected to said control valve means;

control interface means mounted on said support structure, said control interface means operatively interconnecting the pencil and the gas receptacle, wherein input from said operator control means to said control interface means regulates the provision of gas for the gas-enhanced electrosurgery; and accessible outlet means, mounted on said support structure and adapted for connectably receiving said selected standard electrical plug, said outlet means selectively interconnecting said one of said plurality of standard electrosurgical generators to said control interface means.

22. An apparatus, as claimed in claim 21, wherein said first receiving means is contained within said support structure.

23. An apparatus, as claimed in claim 22, wherein said inert gas receptacle is positioned horizontally to fluidly engage with said first receiving means.

24. An apparatus, as claimed in claim 21, wherein said control valve means has at least a first stage and a second stage, said first stage preventing the flow of inert gas to said electrosurgical pencil, said second stage allowing the flow of inert gas to said electrosurgical pencil at a predetermined rate.

25. An apparatus, as claimed in claim 21, wherein said operator control means comprises a foot activated switch.

26. An apparatus, as claimed in claim 21, wherein said operator control means comprises at least one selectable switch positioned on the electrosurgical pencil.

27. An apparatus, as claimed in claim 21, wherein said operator control means comprises two selectable switches positioned on the electrosurgical pencil, the activation of said first switch initiating the provision of a first electrical output to the electrosurgical pencil, the activation of said second switch initiating a second electrical output and the provision of inert gas to the electrosurgical pencil.

28. An apparatus, as claimed in claim 27, wherein said second switch is two-stage, the activation of said first stage providing said second electrical output to the electrosurgical pencil and the activation of said second stage providing inert gas to the electrosurgical pencil.

* * * * *